(12) United States Patent
Shigetou et al.

(10) Patent No.: US 6,303,757 B1
(45) Date of Patent: *Oct. 16, 2001

(54) INDIRECT POLYMERIZED AND LABELLED ANTIBODY AND METHOD FOR MANUFACTURING THE SAME

(75) Inventors: Nobuyuki Shigetou, Hirakata; Jinsei Miyazaki, Higashiosaka, both of (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/305,289

(22) Filed: May 5, 1999

Related U.S. Application Data

(63) Continuation-in-part of application No. 08/831,204, filed on Apr. 2, 1997, now Pat. No. 5,922,618, and a continuation-in-part of application No. 08/745,337, filed on Nov. 8, 1996, now Pat. No. 5,965,713.

(30) Foreign Application Priority Data

May 7, 1998 (JP) .................................................. 10-125004

(51) Int. Cl.$^7$ .............................. C07K 17/02; C07K 1/13; G01N 33/533
(52) U.S. Cl. ................... 530/391.5; 436/800; 530/391.3; 530/402; 530/404; 530/405
(58) Field of Search .............................. 530/391.3, 391.5, 530/402, 405, 404; 436/800

(56) References Cited

U.S. PATENT DOCUMENTS

| | | |
|---|---|---|
| 5,650,334 | 7/1997 | Zuk et al. . |
| 5,922,618 | * 10/1999 | Shigetou et al. ...................... 436/532 |
| 5,965,713 | * 10/1999 | Shigeto et al. ......................... 530/402 |

FOREIGN PATENT DOCUMENTS

| | | |
|---|---|---|
| WO 90/07118 A2 | 6/1990 | (EP) . |
| 0800083A | 10/1997 | (EP) . |
| 08259826 A | * 10/1996 | (JP) . |
| 09132725 | 5/1997 | (JP) . |

OTHER PUBLICATIONS

Mujumdar et al, Bioconjugate Chemistry, 4 (2), 105, 1993.*
Bajyanason et al, Derwent–Acc–No.: 1990–224610, 1993.*

* cited by examiner

*Primary Examiner*—Mary E. Ceperley
(74) *Attorney, Agent, or Firm*—McDermott, Will & Emery

(57) ABSTRACT

A high-sensitive indirect polymerized and labelled antibody is disclosed. The antibody facilitates detection of a low concentration of antigen as an analyte in a sample solution. The indirect polymerized and labelled antibody of the present invention is prepared by polymerizing an antibody using a multi-functional reagent, binding the polymerized antibody with a protein via a disulfide bond of the antibody to form a polymerized antibody conjugate, and labelling the conjugate with a cyanine dye represented by the following formula:

(2)

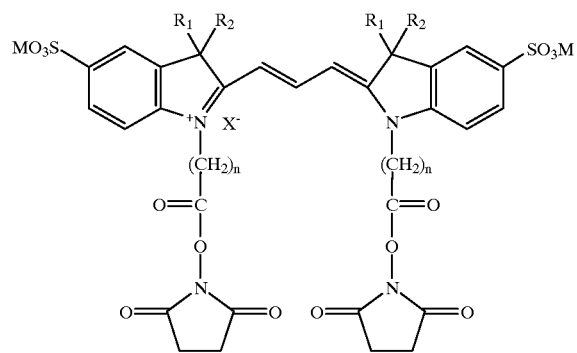

where $R_1$ and $R_2$ represent hydrogen or an alkyl group, X represents a halogen, M represents hydrogen or an alkali metal, and n represents an integer of 1 to 4.

3 Claims, 1 Drawing Sheet

INDIRECT POLYMERIZED AND LABELLED ANTIBODY AND METHOD FOR MANUFACTURING THE SAME

CROSS-REFERENCE TO RELATED APPLICATIONS

This application is a continuation-in-part of application Ser. No. 08/831,204 filed Apr. 2, 1997, now U.S. Pat. No. 5,922,618 and a continuation-in-part of application Ser. No. 08/745,337 filed Nov. 8, 1996, now U.S. Pat. No. 5,965,713.

BACKGROUND OF THE INVENTION

The present invention relates to an polymerized and labelled antibody prepared by polymerizing an antibody and binding the resultant polymerized antibody to a protein to form a protein complex or polymerized antibody conjugate, and labelling the conjugate with a cyanine dye, and further to a method for manufacturing the same.

A dye-labelled antibody prepared by labelling an antibody with a dye, which is visible optically, has a specific reaction with an immunogen or antigen contained in a sample solution. Therefore, such antibody has been used, for example, in an immunosensor for detecting a specific substance or antigen contained in a sample solution with the aid of immunological antigen-antibody reaction and has a wide application as a diagnostic means at various medical facilities.

Cyanine dyes are the most frequently used dyes for labelling antibodies, because they are highly reactive and have a high molar absorption coefficient (see Bioconjugate Chemistry Vol. 4, No. 2, pp. 105–111, 1993).

Those cyanine dyes have a functional group which reacts with an amino group or a carboxyl group present in the antibody and forms a covalent bond. The binding ratio of cyanine dye to antibody is 20 to 50 molecules per molecule of antibody.

The cyanine dye-labelled antibody thus produced has been applied to, for example, immunochromatography because of its generally high visibility and widely used for detecting a small amount of a specific substance such as human chorionic gonadotropin which is contained only in the urine of pregnant women.

Normal antibody includes several hundreds to several thousands of amino group or carboxyl group. However, the conventional interpretation is that, of those many amino or carboxyl groups, only 50 or so can participate in the reaction due to its three-dimensional structure, which limits the number of binding molecules of cyanine dye to 50 molecules per molecule of antibody.

Moreover, since the antibody has a limited number of reaction site with antigen only to 2 for one molecule, the binding sensitivity of antibody to antigen remains low.

The use of such a labelled antibody in an immunosensor or the like limits the sensitivity of the sensor, producing a significant problem of difficult detection of analyte, that is, antigen if its concentration in a sample solution is low.

In view of the above-mentioned problems, the object of the present invention is to provide a high-sensitive indirect polymerized and labelled antibody facilitating detection of a low concentration of analyte in a sample solution.

Another object of the present invention is to provide a method for manufacturing the polymerized and labelled antibody as stated above.

BRIEF SUMMARY OF THE INVENTION

The present invention provides an polymerized and labelled antibody comprising an antibody and a dye for labelling the antibody, the dye being a cyanine dye represented by one of the chemical formulae (1) to (4):

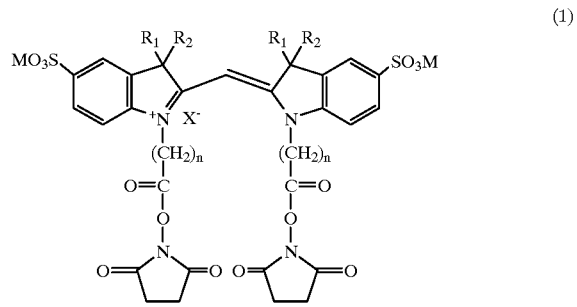

(1)

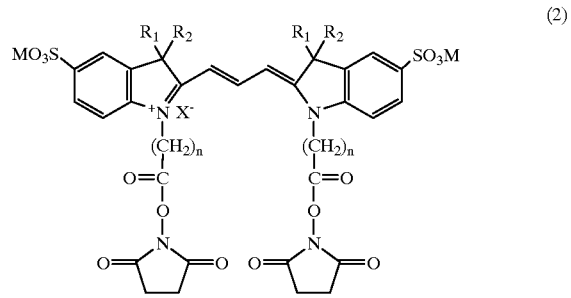

(2)

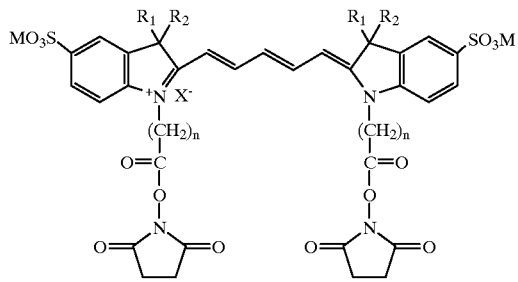

(3)

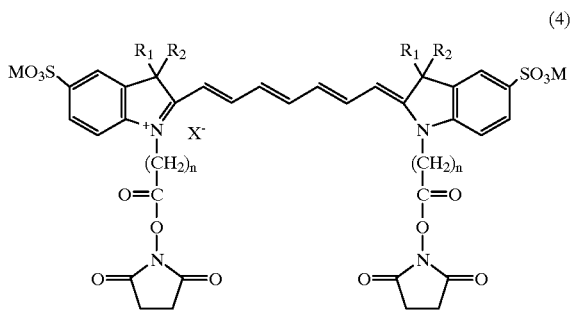

(4)

where $R_1$ and $R_2$ represent hydrogen or an alkyl group, X represents a halogen, M represents hydrogen or an alkali metal, and n represents an integer of 1 to 4, wherein the antibody is polymerized via a multi-functional reagent and bound to a protein via a disulfide bond to form a polymerized antibody conjugate, the antibody conjugate being labelled with the cyanine dye.

A polymerized antibody prepared by polymerizing an antibody is multi-valent having many reaction sites with antigen and therefore has a high binding sensitivity to antigen compared to other usual divalent antibodies.

Moreover, when bound to a protein, the resultant polymerized antibody conjugate is increased in area for binding to the cyanine dye, which also increases the number of binding molecules of the dye to the polymerized antibody conjugate. As a result, the polymerized and labelled antibody obtained by the above-mentioned method can have excellent visibility.

The use of the polymerized and labelled antibody in accordance with the present invention in, for example, immunochromatography facilitates detection of a low concentration of analyte, that is, antigen with high sensitivity. The polymerized and labelled antibody in accordance with the present invention is also applicable to any type of biosensor because of its high sensitivity.

In a preferred mode of the present invention, the polymerized and labelled antibody has a structure where the skeleton of the cyanine dye is bound to the polymerized antibody conjugate via a covalent bond between acylcarbon derived from a succinimidyl group present in the cyanine dye and nitrogen derived from an amino group present in the polymerized antibody conjugate.

In the polymerized and labelled antibody in accordance with the present invention, desirable degrees of polymerization for the antibody may be in a range of 2 to 50.

The method for manufacturing the polymerized and labelled antibody in accordance with the present invention comprises the steps of polymerizing an antibody using a multi-functional reagent in a neutral or weak alkaline phosphate buffer solution to form a polymerized antibody, reducing a protein in a neutral or weak alkaline phosphate buffer solution to form a reduced protein, reacting the polymerized antibody with the reduced protein to form a polymerized antibody conjugate, and reacting the polymerized antibody conjugate with a dye thereby labelling the polymerized antibody conjugate with the dye, the dye being a cyanine dye represented by one of the chemical formulae (1) to (4).

In another mode of the present invention, the method may comprise the steps of polymerizing an antibody using a multi-functional reagent in a neutral or weak alkaline phosphate buffer solution to form a polymerized antibody, reducing a protein in a neutral or weak alkaline phosphate buffer solution to form a reduced protein, reacting the reduced protein with a dye to form a labelled protein, and reacting the polymerized antibody with the labelled protein, the dye being a cyanine dye represented by one of the above-mentioned chemical formulae (1) to (4).

In either method, preferable pH value for the phosphate buffer solution is in a range of 7.0 to 8.0.

Applicable antibodies to the polymerized and labelled antibody in accordance with the present invention are not limited to particular ones and any antibody can be used regardless of its derivation and subclass. Examples of applicable antibodies are a variety of immunoglobulin (Ig) such as mouse IgG, mouse IgM, mouse IgA, mouse IgE, rat IgG, rat IgM, rat IgA, rat IgE, rabbit IgG, rabbit IgM, rabbit IgA, rabbit IgE, goat IgG, goat IgM, goat IgE, goat IgA, sheep IgG, sheep IgM, sheep IgA, sheep IgE, etc. These antibodies may be commercially available or harvested directly from the animal of interest.

The multi-functional reagent may be exemplified as reagents having, in the same molecule, 2 or more functional groups, such as succinimidyl group, pyridildisulfide group, etc., which can bind to an antibody. Examples of such reagent may be dithiosulfosuccinimidyl propionate represented by the chemical formula (5), bis(sulfosuccinimidyl) suberate represented by the chemical formula (6), disuccin- imidyl tartrate represented by the chemical formula (7), ethylene glycol bis(succinimidyl succinate) represented by the chemical formula (8), N-succinimidyl-3-(2-pyridildithio)propionate represented by the chemical formula (9), etc.

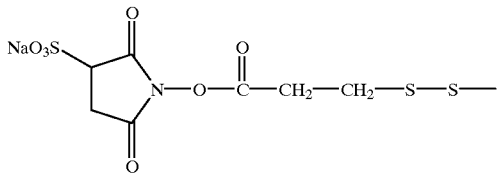

(5)

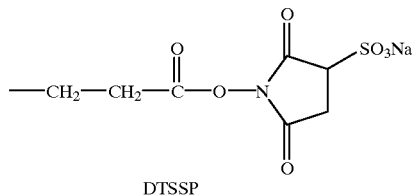

DTSSP (6)

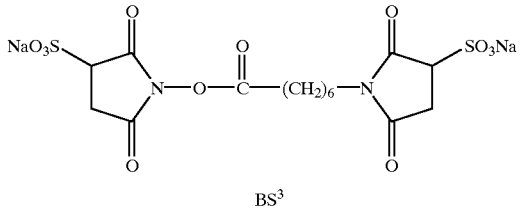

BS³

(7)

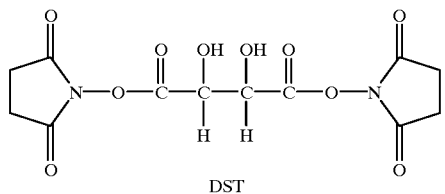

DST (8)

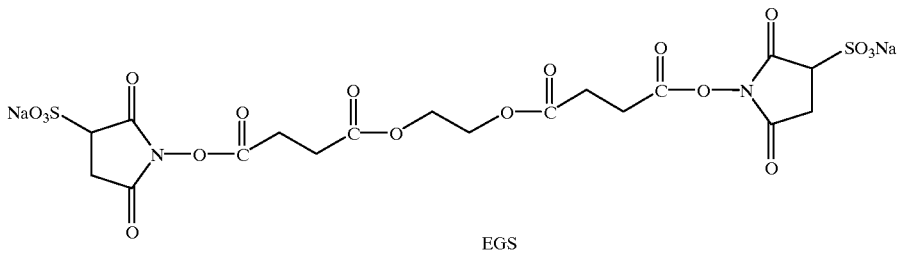

EGS (9)

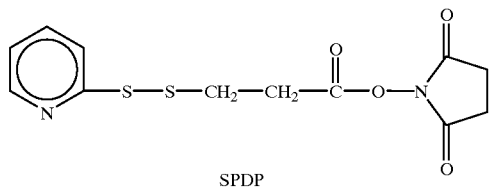

SPDP

The protein to be bound to the polymerized antibody may be any one that does not function as an antibody. Highly water-soluble protein is more preferable. For example, serum-derived albumin is preferable because it has no inhibitory effect on the antigen-antibody reaction and is highly soluble in water.

Cyanine dyes represented by the chemical formula (1) or (2) are red dyes facilitating macroscopic confirmation.

Whereas the dyes represented by the chemical formula (1) are less in number of covalent carbon and have high solubility in water, those represented by the chemical formula (2) have an intense deep red color and are most easily confirmed macroscopically.

If a device, such as sensor, is used in confirming coloring of the cyanine dye, the color of the dye is not limited to red, and blue dyes represented by the chemical formula (3) or (4) may be used similarly.

The dyes represented by the chemical formula (3) or (4) are less likely to be adversely affected by impurities contained in the sample solution, because their absorption spectrum exists only in the region of long wavelength.

In the chemical formulae (1) to (4), the halogen represented by X may be exemplified as fluorine, chlorine, bromine or iodine, and the metal represented by M may be exemplified as lithium, sodium, potassium or the like.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
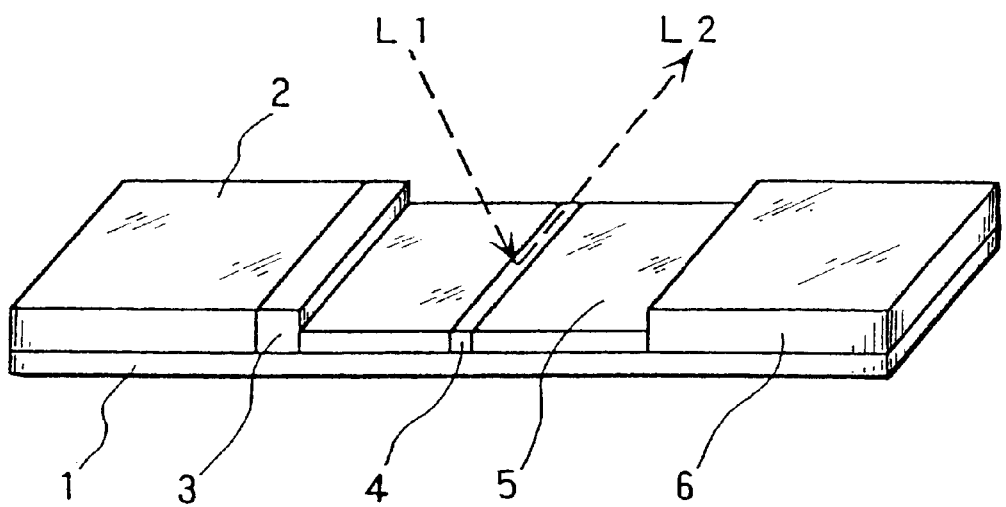
FIG. 1 is an oblique sketch illustrating the structure of immunochromatography used in one example of the present invention.

First, one example of the synthetic pathway of the cyanine dye represented by the formula (2) will be described.

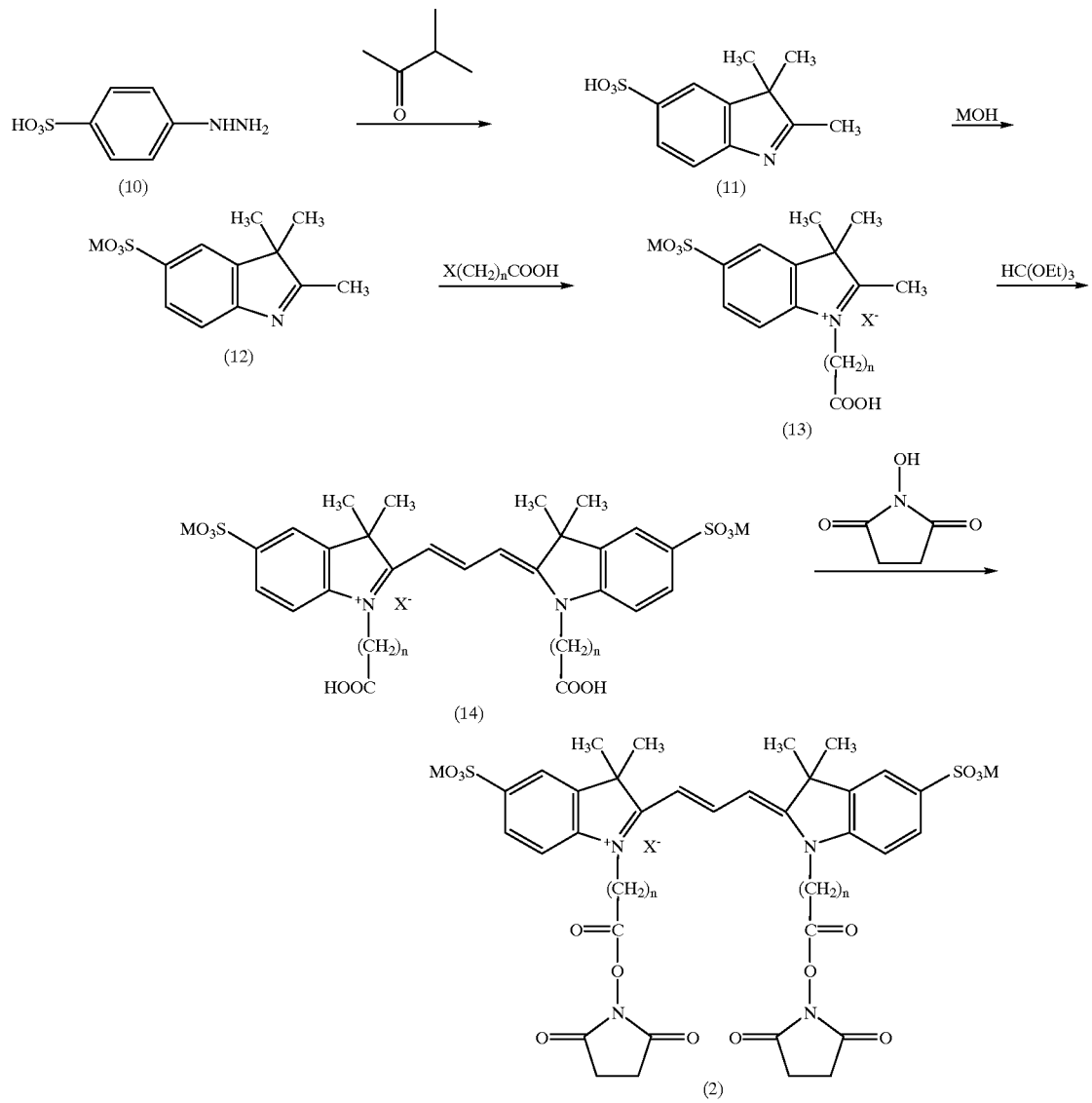

In the first step, hydrazinobenzene sulfonic acid (10) and isopropyl methyl ketone are dissolved in an acidic solvent and heated to form indolenium sulfonate (11). A saturated alcohol solution of metallic hydroxide is added to an alcohol solution of the indolenium sulfonate (11) to form a metallic salt (12) of indolenium sulfonate.

In the next step, a halogenated alkyl acid is added to an organic solvent of the metallic salt (12) and heated to form another metallic salt (13) of carboxylalkyl indolenium sulfonate. Here, it is preferable for the halogenated alkyl acid to have 1 to 4 carbon atoms in consideration of its solubility in water.

The halogen contained in the compounds represented by the chemical formulae (1) to (4), (13) and (14) may be exemplified as fluorine, chlorine, bromine, or iodine. The metal contained in the compounds represented by the chemical formulae (1) to (4), and (12) to (14) may be exemplified as lithium, sodium, potassium or the like.

In the following, the mechanism of polymerization reaction of the antibody using a multi-functional reagent will be described.

(15)

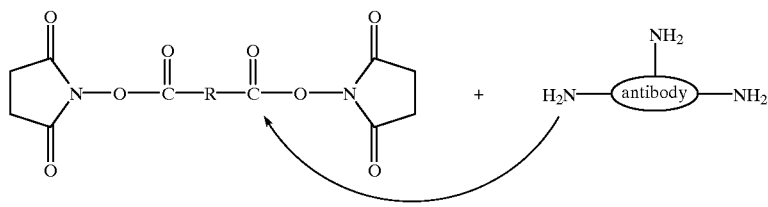

(16)

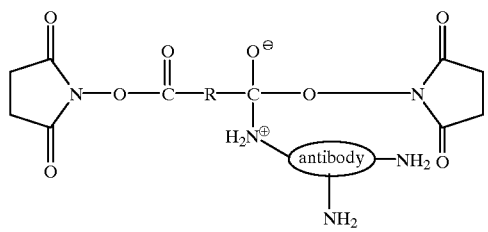

(17)

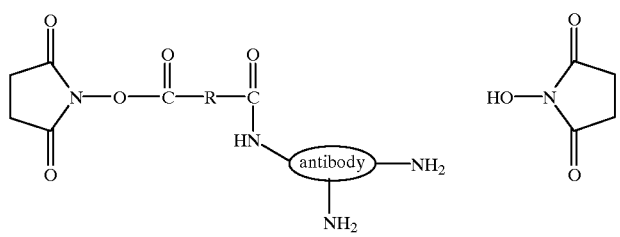

(18)

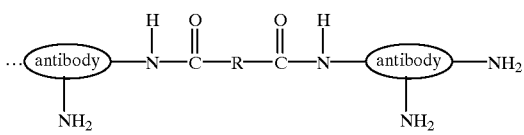

In the last step, the metallic salt (13) and ethyl orthoformate are dissolved in a basic organic solvent and heated to form a carboxylic acid derivative (14). Then, hydroxysuccinimide is added to an organic solvent of the carboxylic acid derivative (14) together with dicyclohexylcarbodiimide as a condensing agent and the mixture is stirred which finally produces a cyanine dye represented by the chemical formula (2) for use as a labelling dye.

In the synthesis of the cyanine dyes represented by the chemical formula (1), N-carboxyethyl-3,3-dimethylindolenine is used in place of the above-mentioned ethyl orthoformate. Similarly, in the synthesis of the cyanine dyes represented by the chemical formula (3) or (4), tetramethoxypropane or glutaconaldehyde tetramethylacetal is used, respectively, in place of the above-mentioned ethyl orthoformate.

Initial reaction is such that, as shown in the formula (15), when a multi-functional reagent, dithiobis (sulfosuccinimidyl propionate) which has 2 or more succinimidyl groups is added to an antibody, access of an amino group of the antibody toward an ester bond of one of the succinimidyl groups of the multi-functional reagent may take place as shown in the formula (16).

Subsequently, reaction between the amino group and the ester bond will take place and the amino group loses one hydrogen atom as shown in the formula (17). Then, the free hydrogen atom released from the amino group binds to the succinimide of the succinimidyl group and converts the succinimide to hydroxysuccinimide, resulting in a release of the hydroxysuccinimide out of the succinimidyl group. While the above reaction proceeds, the residue of the succinimidyl group and the amino group which has been deprived of one hydrogen atom bind to each other to form an amide bond, which in turn functions to bind the molecule of the multi-functional reagent to the molecule of the antibody.

The same reaction also occurs in the remaining succinimidyl groups of the multi-functional reagent to form another amide bond for binding other molecule of the multi-functional reagent to other molecule of the antibody as shown in the formula (18). This reaction is repeated and a polymerized antibody is formed.

The binding mechanism between the cyanine dye having succinimidyl groups and the antibody having amino groups is similar to that as shown above.

In the following, the present invention will be described more specifically by way of concrete examples.

(I) Synthesis of Polymerized Antibody 10 mg mouse IgG (corresponding to $6.667 \times 10^{-5}$ mmol) was dissolved in 1 ml phosphate buffer solution (hereinafter abbreviated to "PBS"). Then, a drop (0.1 ml) of PBS containing dithiosulfosuccinimidyl propionate (hereinafter abbreviated to "DTSSP") was added to the mouse IgG PBS while stirring it at 35° C. The PBS of DTSSP used here contained DTSSP at 4.057 mg (corresponding to 0.006667 mmol, 100 equivalent weights).

Then, after stirring for 30 min at 35° C., the mixture was gel-filtered using a Sepharose gel (trade name: Sephadex G25M column) which gave about 6 ml PBS of IgG aggregation (IgGagg.). The concentration of one IgG molecule in the IgG aggregation, that is, IgGagg. was calculated as follows:

The solution (0.5 ml) thus synthesized was measured for the absorbance at 280 nm and was found to have an absorbance of 2.69. Since the absorption at 280 nm as observed was considered to have derived from IgG, the concentration of IgG aggregation, that is, IgGagg. can be determined as follows:

$$IgGagg. = 2.69/2.099 \times 10^5 = 1.282 \times 10^{-5} (M).$$

At calculation, the molar absorption coefficient of IgG at 280 nm was defined as $2.099 \times 10^5$.

(II) Synthesis of Polymerized Antibody Conjugate

Bovine serum albumin (hereinafter abbreviated to "BSA") (110 mg corresponding to 0.001667 mmol, 25 equivalent weights of IgG) was dissolved in 5 ml PBS and dithiothreitol (77 mg) was further added to the resultant mixture and stirred for 30 min at room temperature to reduce the BSA. The solution was then gel-filtered using a Sephadex G25M column (2.5×30 cm), which gave 28 ml PBS of BSA (SH active).

To the PBS of BSA thus obtained, 6 ml PBS of the polymerized antibody produced in the above Item (I) was added and stirred at 4° C. overnight, and then gel-filtered using a Sepharose gel (trade name Sephacryl S300HR column), which gave 50 ml PBS of polymerized antibody conjugate.

(III) Preparation of Polymerized and Labelled Antibody

A dye represented by the chemical formula (2) and referred to as "SLIC3" was dissolved in 0.2 ml PBS at 350.2 mg (corresponding to 0.34 mmol, 200 equivalent weights of the total protein content). The resultant solution was gently added drop by drop in 50 ml PBS of the polymerized antibody conjugate produced in the above Item (II). In the dye used here, X is iodine, M is potassium and n is 2 in the chemical formula (2).

After stirring at 4° C. for 20 hours, the solution was gel-filtered using a Sephadex G25M column (2.5×30 cm, 2.5×150 cm), which gave 64 ml PBS of polymerized and labelled antibody). For the polymerized and labelled antibody thus obtained, the number of SLIC3 molecules per IgG molecule was determined as follows:

The solution was measured for the absorbance at 550 nm in the same manner as described previously, and was found to have an absorbance of 24.7. Since the polymerized antibody conjugate is not absorbed at 550 nm, the absorption as observed was considered to have derived from the SLIC3 molecules bound to the polymerized antibody conjugate. Therefore, the concentration of SLIC3 [SLIC3] can be determined as follows:

$$[SLIC3] = 24.7/8.55 \times 10^4 = 2.889 \times 10^{-4} (M).$$

At calculation, the molar absorption coefficient of SLIC3 at 550 nm was defined as $8.55 \times 10^4$.

Therefore, the number of molecules of SLIC3 bound to one IgG molecule of the polymerized and labelled antibody can be determined as follows:

$$[SLIC3]/[IgGagg.] = 2.889 \times 10^{-4}/1.042 \times 10^{-6} = 277.3 \text{ molecules}.$$

At calculation, the concentration of one molecule of IgG bound to the protein, that is [IgGagg.] was defined as 10 mg/64 ml ($1.042 \times 10^{-6}$M).

(IV) Evaluation of Polymerized and Labelled Antibody

The polymerized and labelled antibody produced in the above Item (III) was introduced in an immunochromatosensor. The sensitivity of this antibody was assessed by measuring the absorbance at 550 nm.

FIG. 1 is an oblique sketch illustrating the structure of the immunochromatosensor used here. A first glass filter 2, an antibody fixer film 5 made of nitrocellulose and a second glass filter 6 are arranged in this order on a supporting plate 1 made of a plastic such as polyvinyl chloride. The first glass filter 2 is impregnated with the polymerized and labelled antibody produced in Item (III) at one end portion which is in contact with the antibody fixer film 5 to form a labelled antibody-impregnated area 3. Another antibody which can react with the same antigen as that of the indirect polymerized and labelled antibody is fixed by adsorption at a predetermined site of the antibody fixer film 5 to form an antibody-fixed area 4.

The absorbance of the polymerized and labelled antibody in accordance with the present invention was measured using an immunochromatosensor having the above-mentioned structure. One method of measurement is as follows:

By the principle of chromatography, when drops of a sample solution are added to the other end of the first glass filter 2 which is not contact with the antibody fixer film 5, the sample solution starts to move from the first glass filter 2 toward the second glass filter 6 passing the labelled antibody-impregnated part 3. At that time, the indirect polymerized and labelled antibody at the labelled antibody-impregnated area 3 binds to the antigen contained in the sample solution. Then, the sample solution containing the polymerized and labelled antibody bound to the host antigen moves toward the antibody-fixed area 4 and binding of the host antigen to the fixed antibody at the antibody-fixed area 4 takes place to fix the antigen at the antibody-fixed area 4. The remaining sample solution continues to move toward the second glass filter 6 passing the antibody fixer film 5 and is finally absorbed in the second glass filter 6.

The absorbance was determined by irradiating a light L1 having a wavelength of 550 nm to the antibody-fixed area 4 and measuring a reflected light L2.

Then, other polymerized and labelled antibodies were produced in the same manner as described above, except for the use of cyanine dyes represented by the chemical formulae (1), (3) and (4) in place of that represented by the chemical formula (2). The antibodies thus produced were applied to an immunochromatosensor and measured for their absorbance at 430, 640 and 720 nm, respectively. In the dyes used here, X is iodine, M is potassium and n is 2 in the chemical formulae (1), (3) and (4).

For comparison, another labelled antibody was produced in the same manner as described above, except for the use of non-polymerized antibody in place of polymerized antibody conjugate, and similarly applied to an immunochromatosensor to measure its absorbance.

The results showed an absorbance of about 0.8 for the examples of the polymerized labelled antibody in accordance with the present invention each of which includes a polymerized antibody conjugate, and an absorbance of about 0.08 for the labelled antibody of the comparative example including only a non-polymerized antibody. The results indicate that the sensitivity of the polymerized and labelled antibody in accordance with the present invention is about 10-fold the sensitivity of the comparative example.

As discussed above, the polymerized and labelled antibody in accordance with the present invention have many reaction sites with an antigen and are rich in number of binding molecules of the dye to one molecule of the antibody, and therefore facilitates immunological detection with high sensitivity. The use of the polymerized and labelled antibody in accordance with the present invention in, for example, immunochromatography, therefore, enables production of a high-sensitive sensor.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A polymerized antibody conjugate labeled with a cyanine dye comprising an polymerized antibody and a dye for labeling said antibody, said dye being a cyanine dye represented by one of the following chemical formulae (1) to (4):

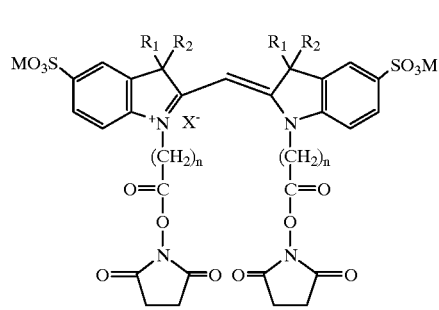

(1)

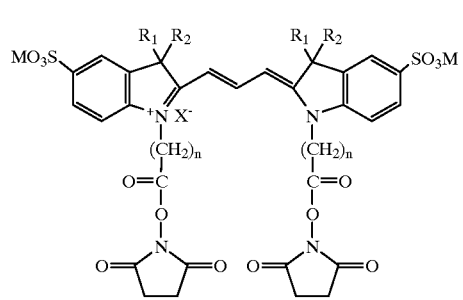

(2)

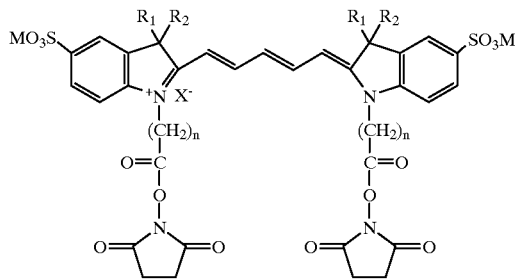

(3)

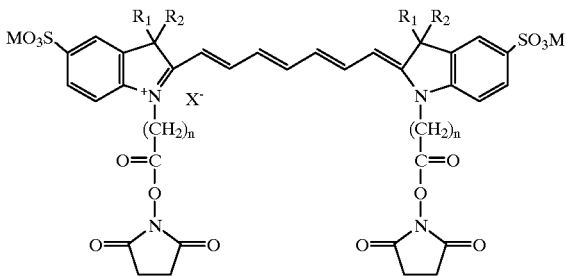

(4)

where $R_1$ and $R_2$ represent hydrogen or an alkyl group, X represents a halogen, M represents hydrogen or an alkali metal, and n represents an integer of 1 to 4, wherein said antibody is polymerized via a multi-functional reagent, includes at least one amino group, and is bound to a protein via a disulfide bond to form a polymerized antibody conjugate, said polymerized antibody conjugate being bonded to said cyanine dye through said amino group.

2. The polymerized antibody conjugate labeled in accordance with claim 1, wherein the said cyanine dye is bound to said polymerized antibody conjugate via a covalent bond between acylcarbon derived from a succinimidyl group present in said cyanine dye and nitrogen derived from said amino group present in said polymerized antibody conjugate.

3. A method for manufacturing the a polymerized antibody conjugate labeled with a cyanine dye in accordance with claim 1, comprising the steps of:

polymerizing an antibody using a multi-functional reagent in a neutral or weak alkaline phosphate buffer solution to form a polymerized antibody, reducing a protein in a neutral or weak alkaline phosphate buffer solution to form a reduced protein, reacting said polymerized antibody with said reduced protein to form a polymerized antibody conjugate having at least one amino group, and reacting said polymerized antibody conjugate with a dye to bond said polymerized antibody with said cyanine dye through said amino group, said dye being a cyanine dye represented by one of the chemical formulae (1) to (4):

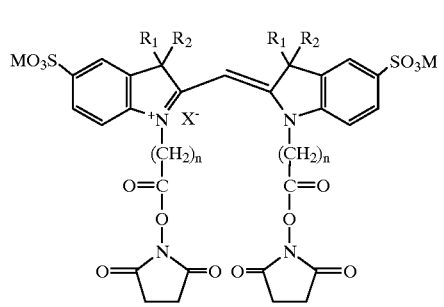
(1)
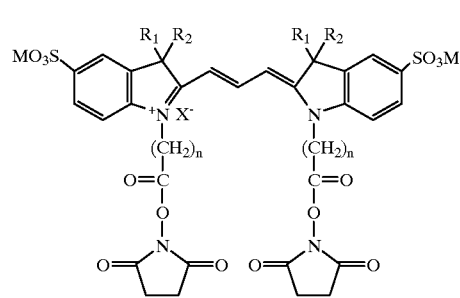
(2)
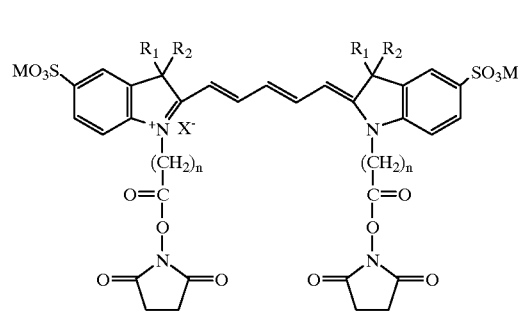
(3)
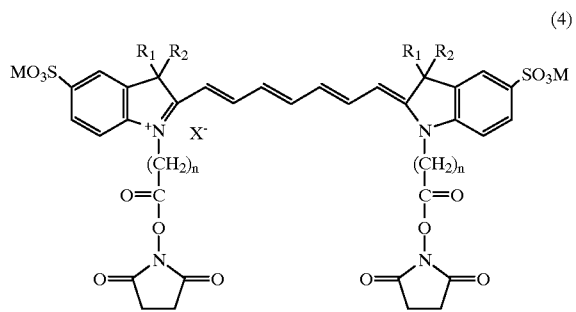
(4)
where $R_1$ and $R_2$ represent hydrogen or an alkyl group, X represents a halogen, M represents hydrogen or an alkali metal, and n represents an integer of 1 to 4.
* * * * *